US006375958B1

(12) United States Patent
Cauwet et al.

(10) Patent No.: US 6,375,958 B1
(45) Date of Patent: *Apr. 23, 2002

(54) COSMETIC COMPOUNDS CONTAINING AT LEAST ONE ANIONIC SURFACTANT OF ALKYLGALACTOSIDE URONATE TYPE AND AT LEAST ONE ORGANOPOLYSILOXANE

(75) Inventors: Daniele Cauwet, Paris; Claude Dubief, Le Chesnay, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/999,666

(22) Filed: Sep. 2, 1997

Related U.S. Application Data

(63) Continuation of application No. 08/556,908, filed as application No. PCT/FR94/00629 on May 31, 1994, now abandoned.

(30) Foreign Application Priority Data

Jun. 1, 1993 (FR) .............................................. 93 06528

(51) Int. Cl.$^7$ ............................................... A61K 7/075
(52) U.S. Cl. .................. 424/401; 424/70.12; 424/70.22
(58) Field of Search ........................... 424/70.12, 70.22, 424/401

(56) References Cited

U.S. PATENT DOCUMENTS

| 4,906,459 A | * | 3/1990 | Cobb et al. ..................... 424/70 |
| 5,308,551 A | * | 5/1994 | Beauquey et al. .......... 252/548 |
| 5,412,118 A | * | 5/1995 | Vermeer et al. ............. 549/417 |
| 5,501,812 A | * | 3/1996 | Vermeer et al. ........ 252/174.17 |
| 5,688,929 A | * | 11/1997 | Petit et al. .................... 536/4.1 |

FOREIGN PATENT DOCUMENTS

| EP | 0 550 276 | | 3/1993 |
| EP | 0 532 370 | | 7/1993 |
| EP | 550 276 | * | 7/1993 |
| FR | 2 679 563 | | 1/1993 |

* cited by examiner

*Primary Examiner*—Margaret G. Moore
(74) *Attorney, Agent, or Firm*—Jacobson Holman, PLLC

(57) ABSTRACT

Cosmetic compositions containing in an aqueous medium an alkylgalactoside uronate and an organopolysiloxane and their use in the treatment or washing of keratinous materials. The alkylgalactoside uronate is based on formula (I):

(I)

[structure of alkylgalactoside uronate with R, OH, H, OR$_1$, and ring carbons]

$R_1$ is a $C_8$–$C_{22}$ alkyl;

(i)

$R$ is $\diagdown$C—CH(OH)—CO$_2$R$_2$ (ii)

or —CH(OH)—CH—CO$_2$R$_2$, with carbon carrying the hydroxyl group being linked to the endocyclic oxygen atom; $R_2$ is hydrogen, an alkaline metal, an alkaline-earth metal or a quaternary ammonium group.

18 Claims, No Drawings

COSMETIC COMPOUNDS CONTAINING AT LEAST ONE ANIONIC SURFACTANT OF ALKYLGALACTOSIDE URONATE TYPE AND AT LEAST ONE ORGANOPOLYSILOXANE

This application is a continuation of application Ser. No. 08/556,908, filed Nov. 29, 1995, abandoned, which is a 371 of PCT/FR94/00629, filed May 31, 1994.

The invention relates to cosmetic compositions containing at least one anionic surfactant of alkylgalactoside uronate type and one organopolysiloxane and to their uses for treating keratinous substances.

Compositions for washing hair or the skin are generally formulated from anionic or nonionic surfactants or their mixtures, optionally in the presence of amphoteric surfactants.

It has been proposed to add silicones to these washing compositions in order to improve their cosmetic properties but the lathering ability of such compositions and the quality of the lathers are unsatisfactory.

Anionic surfactants of alkylgalactoside uronate type have already been recommended in washing compositions for the hair. They have been described in EP 0,532,370.

Compositions for washing the hair which use only these surfactants do not lead to good cosmetic properties; in particular, disentangling of wet hair is difficult and the qualities of the lathers are unsatisfactory.

The Applicant Company has just surprisingly discovered that the combination, in washing and/or treating compositions for keratinous substances, of an anionic surfactant of alkylgalactoside uronate type and of an organopolysiloxane defined below conferred greatly improved disentangling properties for wet hair on these compositions.

Moreover, the combination in accordance with the present invention makes it possible to obtain a copious, compact and very soft lather.

In addition, the Applicant Company has observed that the cosmetic compositions containing such a combination conferred good cosmetic properties, such as softness or a pleasant feel, and that they were very well tolerated by the skin.

The subject of the present invention is therefore cosmetic compositions containing at least one alkylgalactoside uronate and one organopolysiloxane defined below.

Another subject of the invention consists of the use of these compositions for treating and/or washing keratinous substances such as the hair or the skin.

Finally, another subject of the invention consists of a cosmetic treatment process for the hair or for the skin by means of the compositions of the invention; washing and treatment processes for the hair being preferred.

The cosmetic compositions according to the invention contain, in a cosmetically acceptable aqueous medium:

(A) at least one anionic surfactant of alkylgalactoside uronate type of formula:

(I)

in which:

$R_1$ denotes a linear or branched alkyl radical containing 8 to 22 carbon atoms, R denotes a group (i)

$$\diagdown CH-CH(OH)-CO_2R_2 \text{ or}$$

(ii)

$$-CH(OH)-CH-CO_2R_2,$$

in which the carbon carrying the hydroxyl group is connected to the endocyclic oxygen atom; $R_2$ being hydrogen, an alkali-metal, an alkaline-earth metal or a quaternary ammonium group which is unsubstituted or substituted by alkyl or hydroxyalkyl radicals or derived from amino acids, (B) at least one organopolysiloxane chosen from:

(i)—organopolysiloxane oils with the exception of linear polydimethylsiloxanes with a viscosity of less than $10^{-1}$ $m^2/s$, (ii)—organopolysiloxane gums, (iii)—organopolysiloxane resins, (iv)—organomodified polysiloxanes, (v)—mixtures of linear polydimethylsiloxanes with a viscosity of less than $10^{-1}$ $m^2/s$ with one or a number of compound(s) defined under (i), (ii), (iii) and (iv).

Anionic surfactants of alkylgalactoside uronate type of formula (I) are known and can be prepared according to the processes described in Patent Application EP-A-0,532,370.

The alkali metal is in particular sodium or potassium and the alkaline-earth metal is preferably magnesium. Mention may be made, as quaternary ammonium salts, of the salts of ammonia, of triethanolamine, of monoethanolamine, of 2-amino-2-methyl-1,3-propanediol or of 2-amino-2-methyl-1-propanol; the amino acid is in particular: histidine, arginine or lysine.

Use is preferably made of the compounds of formula (I) in which the $R_1$ radical denotes a $C_8$–$C_{14}$ alkyl and more particularly the decyl radical.

Use is in particular made of the following compounds:

Sodium decyl α-D-galactopyranoside uronate:

Sodium decyl β-D-galactopyranoside uronate:

Sodium decyl α-D-galactofuranoside uronate:

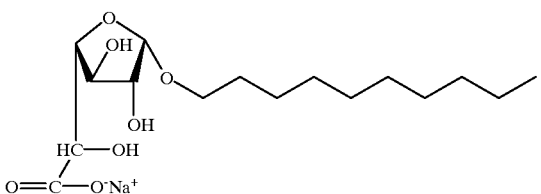

Sodium decyl β-D-galactofuranoside uronate:

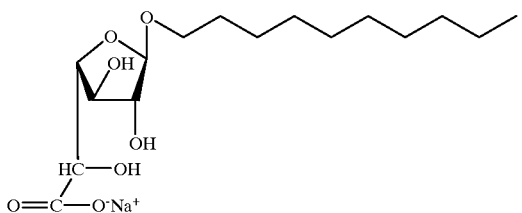

The organopolysiloxanes used in the compositions according to the present invention are organopolysiloxane oils or organosiloxane gums or resins, as such or in the form of solutions in organic solvents or alternatively in the form of emulsions in or of microemulsions.

Among the organosiloxanes used in accordance with the present invention, there may be mentioned, in a non-limiting way:

I. Volatile Silicones

These have a boiling point between 60° C. and 260° C. They are chosen from cyclic silicones containing 3 to 7 silicon atoms and preferably 4 to 5. They are, for example, octamethylcyclotetrasiloxane sold under the name of "Volatile Silicone 7207" by Union Carbide or "Silbione 70045 V2" by Rhône-Poulenc or decamethylcyclopentasiloxane sold under the name of "Volatile Silicone 7158" by Union Carbide, or "Silbione 70045 V5" by Rhône-Poulenc, as well as their mixtures.

There are also mentioned cyclocopolymers of the dimethylsiloxane/methylalkylsiloxane type, such as "Silicone Volatile FZ 3109" sold by the company Union Carbide, which is a dimethylsiloxane/methyloctylsiloxane cyclocopolymer;

II. Nonvolatile Silicones

They consist mainly of polyalkylseiloxanes, polyarylsiloxanes, polyalkylarylsiloxanes, silicone gums and resins and organomodified polysiloxanes, as well as their mixtures.

Among polyalkylsiloxanes, there may mainly be mentioned linear polydimethylsiloxanes with a viscosity greater than $10^{-1}$ m$^2$/s: either, containing trimethylsilyl end groups, such as, for example and in a nonlimiting way, Silbione oils of the 70047 series marketed by Rhône-Poulenc; 47 V 500 000 oil of Rhône-Poulenc or certain Viscasils of General Electric, or containing hydroxydimethylsilyl end groups, such as oils of the 48 V series of Rhône-Poulenc.

In this polyalkylsiloxane class, there may also be mentioned polyalkylsiloxanes sold by the Company Goldschmidt under the names Abilwax 9800 and Abilwax 9801, which are poly($C_1$–$C_{20}$)alkylsiloxanes.

Among polyalkylarylsiloxanes, there may be mentioned linear and/or branched polymethylphenylsiloxanes, polydimethylmethylphenylsiloxanes or polydimethyldiphenylsiloxanes such as, for example:

Rhodorsil 763 oil of Rhône-Poulenc,

Silbione 70641 V 30 and 70641 V 200 oils of Rhône-Poulenc, the product DC 556 Cosmetic Grad Fluid of Dow Corning, silicones of the PK series of Bayer, such as PK20, silicones of the PN or PH series of Bayer, such as PN 1000 and PH 1000, certain oils of the SF series of General Electric, such as SF 1250, SF 1265, SF 1154 or SF 1023.

Silicone gums, in accordance with the present invention, are polydiorganosiloxanes with a high molecular mass of between 200,000 and 1,000,000, used alone or as a mixture in a solvent chosen from volatile silicones, polydimethylsiloxane oils (PDMS), polyphenylmethylsiloxane oils (PPMS), isoparaffins, methylene chloride, pentane, dodecane, tridecane, tetradecane or their mixtures.

There are mentioned, for example, the following compounds:

polydimethylsiloxane,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)].

There may be mentioned, for example, in a non-limiting way, the following mixtures:

1) mixtures formed from a polydimethylsiloxane hydroxylated at the chain ends (Dimethiconol according to the CTFA nomenclature), and from a cyclic polydimethylsiloxane (Cyclomethicone according to the CTFA nomenclature), such as the product Q2 1401 sold by the Company Dow Corning;

2) mixtures formed from a polydimethylsiloxane gum with a cyclic silicone, such as the product SF 1214 Silicone Fluid of General Electric, which is an SE 30 gum with an MW of 500,000 solubilized in SF 1202 Silicone Fluid (decamethylcyclopentasiloxane);

3) mixtures of two PDMSs having a different viscosity, especially of a PDMS gum and of a PDMS oil, such as the products SF 1236 and CF 1241 of the Company General Electric. The product SF 1236 is the mixture of an SE 30 gum defined above having a viscosity of 20 m$^2$/s and of an oil SF 96 having a viscosity of $5.10^{-6}$ m$^2$/s (15% of SE 30 gum and 85% of SF 96 oil).

The product CF 1241 is the mixture of an SE 30 gum (33%) and of a PDMS (67%) having a viscosity $10^{-3}$ m$^2$/s.

Organopolysiloxane resins which can be used in accordance with the invention are crosslinked siloxane systems containing the units: $R_2SiO_{2/2}$, $RSiO_{3/2}$ and $SiO_{4/2}$ in which R represents a hydrocarbon group having 1 to 6 carbon atoms or a phenyl group. Among these products, those particularly preferred are those in which R denotes a lower alkyl radical or a phenyl radical.

Among these resins, there may be mentioned the product sold under the name "Dow Corning 593" or those sold under the names "Silicone Fluid SS 4230" and "SS 4267" by the Company General Electric and which are "dimethyl/trimethylpolysiloxanes".

Organomodified silicones, in accordance with the present invention, are silicones as defined above containing in their general structure one or a number of organofunctional groups attached directly to the siloxane chain or attached via a hydrocarbon radical.

There are mentioned, for example, silicones containing:
a) polyethyleneoxy and/or polypropyleneoxy groups, optionally containing alkyl groups, such as:
the product named dimethicone copolyol sold by the Company Dow Corning under the names DC 1248 and (C12)alkylmethicone copolyol sold by the Company Dow Corning under the name Q2 5200,
Silwet L 722, L 7500, L 77 or L 711 oils of the Company Union Carbide,
the mixture of dimethicone copolyol and of cyclomethicone such as the product sold under the name Q2-3225C by the Company Dow Corning.
b) (per) fluorinated groups such as trifluoroalkyls such as, for example, those sold by the Company General Electric under the names "FF.150 Fluorosilicone Fluid" or by the Company Shin Etsu under the names X-22-819, X-22-820, X-22-821 or X-22-822;
c) hydroxyacylamino groups such as those described in European Patent Application EP-A-0,342,834 and in particular the silicone sold by the Company Dow Corning under the name "Q2-8413";
d) thiol groups such as the silicones X 2-8360 of Dow Corning or GP 72A and GP 71 of Genesee;
e) substituted or unsubstituted amino groups, as in GP4 Silicone Fluid of Genesee, GP 7100 of Genesee, Q2 8220 of Dow Corning, AFL 40 of Union Carbide or the silicone called "Amodimethicone" in the CTFA dictionary;
f) carboxylate groups, such as the products described in European Patent EP 186,507 of Chisso Corporation;
g) hydroxylated groups, such as polyorganosiloxanes containing hydroxyalkyl functional groups, described in French Patent Application No. FR-85 16334, and in particular polyorganosiloxanes containing γ-hydroxypropyl functional groups;
h) alkoxylated groups as in Silicone Copolymer F 755 of SWS Silicones and the products Abilwax 2428, Abilwax 2434 or Abilwax 2440 of the Company Goldschmidt;
i) acyloxyalkyl groups, such as, for example, the polyorganopolysiloxanes described in French Patent Application No. 88 17433, and in particular polyorganosiloxanes containing stearoyloxypropyl functional groups;
j) quaternary ammonium groups, as in the products X2 81 08 and X2 81 09 or the product Abil K 3270 of the Company Goldschmidt;
k) amphoteric or betaine groups, such as in the product sold by the Company Goldschmidt under the name Abil B 9950;
l) bisulfite groups, such as in the products sold by the Company Goldschmidt under the names Abil S 201 and Abil S 255.

The alkylgalactoside uronates of formula (I) are used in the compositions in accordance with the invention in proportions preferably of between 1 and 50% by weight with respect to the total weight of the composition.

The silicones are used in the compositions of the invention in proportions preferably of between 0.01 and 20% by weight with respect to the total weight of the composition.

The compositions in accordance with the invention can additionally contain a thickening agent and/or a suspending agent for the silicone, such as fatty acid alkanolamides, poly(acrylic acid)s, cellulose derivatives, esters of fatty acids and of polyethylene glycol, crosslinked copolymers of acrylamide and of a monomer chosen from ammonium acrylate, partially or totally neutralized 2-acrylamido-2-methylpropanesulfonic acid or methacryloyloxyethyltrimethylammonium chloride; polyetherurethanes, or crosslinked methyl vinyl ether-maleic acid copolymers.

There may also be mentioned, as suspending agent for the silicone, the compounds chosen from
a) those of formula:

$$R_3X \qquad (II)$$

in which $R_3$ is an aliphatic radical with a long carbon chain, optionally interrupted by one or a number of oxygen atoms, and X is a carboxylic, sulfuric or phosphoric acid residue or a radical derived from a carboxylic acid or from an amide; these compounds of formula (II) are chosen from those in which:
(i) $R_3$ is a $C_{11}$–$C_{21}$ alkyl or alkenyl radical; and X is
a COOA group where A is a mono- or polyhydroxyalkyl radical derived from a $C_2$–$C_3$ polyol or a $CH_2CH_2SO_3M$ radical;
a $CO(OCH_2CH_2)_kOH$ group where k has a value between 2 and 150;
a group

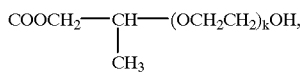

where k has a value between 2 and 150, it being possible for the free OH functional groups of the groups defined above to be esterified with an acid RCOOH where R is a $C_{11}$–$C_{21}$ alkyl or alkenyl;
a $CONR_4R_5$ group where $R_4$ and $R_5$ represent hydrogen or $C_1$–$C_4$ hydroxyalkyl, at least one representing $C_1$–$C_4$ hydroxyalkyl;
an $OSO_3M$ or $1/3PO_4^{3-}M_3$ group where M represents an alkali metal, ammonium or a $C_1$–$C_4$ alkanolamine residue;
(ii) $R_3$ denotes a $R_6O(C_2H_4O)_lCH_2$ radical and X denotes a COOM group where M has the meaning indicated above, $R_6$ denoting a $C_{12}$–$C_{14}$ alkyl radical and l a whole or decimal number between 2.5 and 10, or else $R_6$ denotes oleyl and l varies from 2 to 9 or alternatively $R_6$ denotes $(C_8$–$C_9)$alkylphenyl and l varies from 4 to 8, or the derivatives in which $R_6$ denotes a $(C_{12}$–$C_{16})$alkyl group and X a $CONR_4R_5$ group; in which $R_4$ and $R_5$ have the same meaning as that indicated above and l has a value from 1 to 3 inclusive;
b) amine oxides of formula:

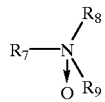

in which $R_7$ denotes a $C_{16}$–$C_{22}$ alkyl group and $R_8$ and $R_9$, which are identical or different, represent a $C_1$–$C_4$ alkyl or $C_1$–$C_4$ hydroxyalkyl group;
c) biopolysaccharides chosen from xanthan gums and scleroglucans.

If the compositions according to the invention are not used for washing keratinous substances, the concentration of anionic surfactants of formula (I) is between 1 and 10% and more particularly between 1 and 5% by weight with respect to the total weight of the composition. These compositions are used in particular as compositions to be rinsed or not to be rinsed, applied before or after shampooing, dyeing, bleaching, perming or hair straightening or in bleaching, dyeing, perming or hair-straightening compositions.

When the compositions according to the invention are washing compositions, they contain the surfactants of formula (I) in a concentration of between 4 and 50% by weight and preferably between 8 and 40% by weight with respect to the total weight of the composition.

The compositions can furthermore contain additional surfactants of anionic, nonionic, amphoteric, zwitterionic or cationic nature.

Among the anionic surfactants, there may be mentioned the alkali metal salts, the ammonium salts, the amine salts, the aminoalcohol salts or the magnesium salts of the following compounds: the fatty acids, alkyl sulfates, alkyl ether sulfates, alkylamidoether sulfates, alkylarylpolyether sulfates or monoglyceride sulfates; the alkylethersulfonates, alkylsulfonates, alkylamidesulfonates, alkylarylsulfonates, olefinsulfonates or paraffinsulfonates; the alkylsulfosuccinates, the alkylethersulfosuccinates or the alkylamidesulfosuccinates; the alkylsulfosuccinamates; the acylglutamates; the alkylsulfoacetates; the alkyl ether phosphates; the acylsarcosinates; the N-acyltaurates; the isethionates; or the alkylamide sulfates.

The alkyl or acyl radical of these various compounds generally consists of a carbon chain containing from 10 to 20 carbon atoms.

It is also possible to use weakly anionic surfactants, such as the polyoxyalkylenated alkyl amide or alkyl ether carboxylic acids, such as those containing 2 to 50 ethylene oxide groups.

The nonionic surfactants are more particularly chosen from the polyethoxylated or polypropoxylated alcohols or α-diols or alkylphenols or fatty acids, with a fatty chain containing 8 to 18 carbon atoms, the number of ethylene oxide or propylene oxide groups being between 2 and 50 and the number of glycerol groups being between 2 and 30.

It is more particularly possible to mention the copolymers of ethylene oxide and of propylene oxide; the condensates of ethylene oxide and of propylene oxide with fatty alcohols; the polyethoxylated fatty amides having preferably 2 to 30 mol of ethylene oxide; the polyethoxylated fatty amines having preferably 2 to 30 mol of ethylene oxide; the oxyethylenated fatty acid esters of sorbitan having preferably 2 to 30 mol of ethylene oxide; the fatty acid esters of sugar, the fatty acid esters of polyethylene glycol, the fatty acid esters of glycols; or the amine oxides such as the oxides of $(C_{10}-C_{14})$alkylamines or of N-acylamidopropylmorpholine.

The preferred amphoteric or zwitterionic surfactants are the derivatives of secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; the $(C_8-C_{20})$ alkylbetaines, the sulfobetaines, the $(C_8-C_{20})$alkylamido $(C_1-C_6)$alkylbetaines or the $(C_8-C_{20})$alkylamido$(C_1-C_6)$ alkylsulfobetaines.

It is also possible to mention the alkylpeptides or the alkylimidazolium betaines.

Among the amine derivatives, there may be mentioned the products marketed under the name Miranol, such as those described in the Patents U.S. Pats. No. 2,528,378 and 2,781,354 or listed in the CTFA dictionary, 3rd edition, 1982, under the names of Amphocarboxyglycinates or of Amphocarboxypropionates.

The cationic surfactants are chosen from the quaternary ammonium salts, such as the $(C_8-C_{22})$ alkyltrimethylammonium halides, the $(C_8-C_{22})$ dialkyldimethylammonium halides or the $(C_8-C_{22})$ alkyldimethylhydroxyethylammonium halides.

The additional cosurfactants can represent up to 50% of the total weight of the surfactants present in the composition.

The pH of the compositions in accordance with the invention is generally between 2 and 10.5 and more particularly between 3 and 8.

Insofar as the cosmetically acceptable medium of the composition according to the invention is an aqueous medium, it may consist solely of water or of a mixture of water and of a cosmetically acceptable solvent, such as $C_1-C_4$ lower alcohols, such as ethanol, isopropanol or n-butanol; alkylene glycols, such as propylene glycol, or glycol ethers.

The compositions in accordance with the invention can be provided in the form of more or less thickened liquids, gels, emulsions (milks or creams), aqueous/alcoholic lotions, dispersions, aerosol foams or solid bars.

The compositions are, for example, emollient lotions, milks or creams, lotions, milks or creams for caring for keratinous substances, make-up removal creams or milks, foundation bases, antisun lotions, milks or creams, lotions, milks or creams for artificial tanning, shaving creams or foams, aftershave lotions, face masks, make-up products for the eyes, colors and foundations for the face, nail varnishes, shampoos, bath or shower products, compositions to be rinsed or not to be rinsed, to be applied before or after shampooing, dyeing, bleaching, perming or hair straightening, or compositions for dyeing, bleaching, perming or straightening the hair.

The compositions in accordance with the invention can also contain, in addition, various additives such as foam reinforcers, sequestering agents, fragrances, electrolytes, fatty substances, such as fatty alcohols, ceramides or mineral, vegetable, animal or synthetic oils or waxes, UV screening agents, agents for combating free radicals, pearlescence agents, biocides, antibacterials, antidandruff agents, antiseborrheic agents, antiparasitic agents, repellents, dyes, pigments, oxidizing agents, reducing agents, moisturizers, anionic and nonionic polymers, vitamins or α-hydroxy acids.

The process for washing and/or for conditioning the keratinous substances and in particular the hair or the skin in accordance with the invention consists in applying at least one composition as defined above to these substances, this application optionally being followed by a stage of rinsing with water.

The washing compositions can be used as shampoos but also as a shower gel for washing the hair and the skin, in which case they are applied to the wet skin and hair, which are rinsed after application.

When the compositions are used for conditioning the hair, they are applied to the wet hair, after which it can either be dried or, after an exposure time of 1 to 10 minutes, rinsed with water. It is observed that the wet hair disentangles readily.

The examples which follow serve to illustrate the invention without, however, having a limiting nature.

EXAMPLE 1

| SHAMPOO | |
|---|---|
| Sodium decyl D-galactoside uronate | 15 g MA |
| Sodium lauryl ether sulfate, $C_{12}/C_{14}$ 70/30, 2.2 EO, as a 28% aqueous solution sold under the name of Empicol ESB/3 FL by Marchon | 5 g MA |

SHAMPOO

| | |
|---|---|
| Polydimethylsiloxane with a MW of 250,000 and a viscosity of 0.5 m²/s | 3 g |
| Xanthan gum, sold under the name of Keltrol T by Kelco | 1 g |
| Dyes, fragrance, preservative | |
| water | q.s. for 100 g |
| pH adjusted to 7 with NaOH | |

The appearance of this shampoo is opalescent and viscous.

EXAMPLE 2

SHOWER GEL

| | |
|---|---|
| Sodium decyl D-galactoside uronate | 20 g MA |
| Sodium N-cocoamidoethyl-N-(ethoxycarboxymethyl)glycinate | 4 g MA |
| α,Ω-Dihydroxylated polydimethylsiloxane/cyclotetra- and cyclopentadimethylsiloxane mixture (56/44) (13/87) sold by Dow Corning under the name of Q2 1041 | 2 g |
| Xanthan gum sold under the name of Keltrol T by Kelco | 0.75 g |
| Dyes, fragrance, preservative | |
| water | q.s for 100 g |
| pH adjusted to 7 with HCl | |

EXAMPLE 3

FOAM BATH

| | |
|---|---|
| Sodium decyl D-galactoside uronate | 25 g MA |
| Sodium lauryl ether sulfate, $C_{12}/C_{14}$ 70/30, 2.2 EO, as a 28% aqueous solution sold under the name of Empicol ESB/3 FL by Marchon | 5 g MA |
| Mixture of polydimethylsiloxane in, 500,000/ and of polydimethylsiloxane - MW 1000 (33/67) sold under the name of CF 1241 by the Company General Electric | 1 g |
| Oxyethylenated (60 EO) tallow ether of myristyl glycol sold under the name of Elfacos GT 282 S by the company Akzo | 2 g |
| Dyes, fragrance, preservative | |
| water | q.s. for 100 g |
| pH ajdusted to 8 with NaOH | |

What is claimed is:

1. Hair washing and/or conditioning cosmetic composition in the form of a thickened liquid, a gel, an emulsion, an aqueous/alcohol lotion, a dispersion or an aerosol foam consisting essentially of, in a cosmetically acceptable aqueous medium:

(A) at least one anionic surfactant of alkylgalactoside uronate type of formula:

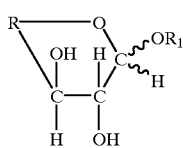

(I)

in which:

$R_1$ denotes a linear or branched $C_8-C_{22}$ alkyl radical,

R denotes a group

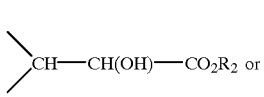

(i)

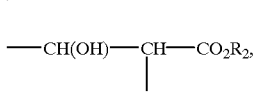

(ii)

in which the carbon carrying the hydroxyl group is connected to the endocyclic oxygen atom; $R_2$ denotes a hydrogen, an alkali metal, an alkaline-earth metal or a quaternary ammonium group which is unsubstituted or substituted by alkyl or hydroxyalkyl radicals or amino acid radicals, and (B) at least one organopolysiloxane selected from the group consisting of:
(i) poly($C_1-C_{20}$)alkylsiloxane oils, linear polydimethylsiloxane oils containing trimethylsilyl end groups and linear polydimethylsiloxane oils containing hydroxydimethylsilyl end groups, with a viscosity greater than $10^{-1}$ m²/s;
(ii) linear and/or branched polymethylphenylsiloxane oils, polydimethylphenylsiloxane oils and polydimethyldiphenylsiloxane oils;
(iii) organopolysiloxane gums with a molecular mass of between 200,000 and 1,000,000 used alone or in the form of a mixture in a solvent, said solvent being selected from the group consisting of the following polymers and copolymers:
polydimethylsiloxane,
poly[(dimethylsiloxane)/(methylvinylsiloxane)],
poly(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)];
(iv) organopolysiloxane resins containing units $R_2SiO_{2/2}$, $RSiO_{3/2}$ and $SiO_{4/2}$ in which R represents a hydrocarbon group having 1 to 6 carbon atoms or a phenyl group; and
(v) modified organopolysiloxanes having in their general structure one or a number of organofunctional group(s) attached directly to the siloxane chain or attached via a hydrocarbon radical, said organofunctional group(s) being selected from the group consisting of:
a) polyethylenoxy and/or polypropylenoxy groups, optionally containing alkyl groups;
b) (per)fluorinated groups;
c) hydroxyacylamino groups;
d) thiol groups;
e) substituted or unsubstituted amino groups;
f) carboxylate groups;
g) hydroxylated groups;
h) alkoxylated groups;
j) quaternary ammonium groups;
k) amphoteric and betaine groups; and
l) bisulfite groups.

2. Composition according to claim 1 wherein $R_2$ is selected from the group consisting of sodium, potassium, magnesium and quaternary ammonium groups selected from the group consisting of ammonium, triethanolammonium, monoethanol ammonium, 2-ammonio-2-methyl-1,3-propanediol, 2-methyl-2-ammonio-1-propanol, histidinium, argininium and lysinium.

3. Composition according to claim 1 in which $R_1$ is a $C_8$–$C_{14}$ alkyl.

4. Composition according to claim 1 in which $R_1$ is the decyl radical.

5. Composition according to claim 4 wherein the compound of the formula (I) is selected from the group consisting of:
- sodium decyl-α-D-galactopyranoside uronate,
- sodium decyl-β-D-galactopyranoside uronate,
- sodium decyl-α-D-galactofuranoside uronate, and
- sodium decyl-β-D-galactofuranoside uronate.

6. Composition according to claim 1 wherein the anionic surfactants of formula (I) are present in proportions of between 1 and 50% by weight and in that the organopolysiloxanes are present in proportions of between 0.01 and 20% by weight; the percentages by weight being expressed with respect to the total weight of the composition.

7. Composition for conditioning keratinous substances according to claim 1 wherein the concentration of anionic surfactants of formula (I) is between 1 and 10% by weight with respect to the total weight of the composition.

8. Composition for washing keratinous substances according to claim 1 wherein the concentration of anionic surfactants of formula (I) is between 4 and 50% by weight with respect to the total weight of the composition.

9. Composition according to claim 1 further comprising an additional anionic, nonionic, amphoteric or cationic cosurfactant in a proportion representing up to 50% of the total weight of surfactants present in the composition.

10. Composition according to claim 9 wherein the additional anionic cosurfactant is selected from the group consisting of the alkali metal salts, the ammonium salts, the amine and aminoalochol salts and the magnesium salts of the compounds: fatty acids; alkyl sulfates, alkyl ether sulfates, alkylamidoether sulfates, alkylarylpolyether sulfates, monoglyceride sulfates and alkylamide sulfates; alkylsulfonates, alkylethersulfonates, alkylsulfosuccinates, alkylethersulfosuccinates and alkylamidesulfosuccinates; acylglutamates; alkylsulfosuccinamates; alkylsulfoacetates; alkyl ether phosphates; acylsarcosinates; N-acyltaurates; and isethionates; the alkyl or acyl radical consisting of a carbon chain containing from 10 to 20 carbon atoms or else polyoxyalkylenated alkyl amide or alkyl ether carboxylic acids.

11. Composition according to claim 9 wherein the nonionic cosurfactant is selected from the group consisting of the polyethoxylated and polypropoxylated alcohols, α-diols, alkylphenols and fatty acids, with a fatty chain containing 8 to 18 carbon atoms, the number of ethylene oxide or propylene oxide groups being between 2 and 50 and the number of glycerol groups being between 2 and 30; the copolymers of ethylene oxide and of propylene oxide; the condensates of ethylene oxide and of propylene oxide with fatty alcohols; the polyethoxylated fatty amides; the polyethoxylated fatty amines; the fatty acid esters of sugar; the fatty acid esters of polyethylene glycol; the fatty acid esters of glycols; and the amine oxides.

12. Composition according to claim 9 wherein the additional amphoteric or zwitterionic cosurfactant is selected from the group consisting of the derivatives of secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; the ($C_8$–$C_{20}$)alkylbetaines, the sulfobetaines, the ($C_8$–$C_{20}$) alkylamido($C_1$–$C_6$)alkylbetaines and the ($C_8$–$C_{20}$) alkylamido($C_1$–$C_6$)alkylsulfobetaines; the alkylpeptides and the alkylimidazoliumbetaines.

13. Washing composition according to claim 9 wherein the additional cationic cosurfactant is selected from quaternary ammonium salts.

14. Composition according to claim 1 which additionally contains a thickening and/or a suspending agent for the organopolysiloxane.

15. Composition according to claim 14 wherein the thickening agent and/or the suspending agent is selected from the group consisting of fatty acid alkanolamides; poly(acrylic acid)s; cellulose; esters of fatty acids and of polyethylene glycol; crosslinked copolymers of acrylamide and of a monomer selected from the group consisting of ammonium acrylate, 2-acrylamido-2-methylpropanesulfonic acid and methacryloyloxyethyltrimethylammonium chloride; polyurethanes; crosslinked methyl vinyl ether-maleic acid copolymers; and the following compounds:

a) those of formula:

$$R_3X \qquad (II)$$

where $R_3$ is an aliphatic radical with a long carbon chain, optionally interrupted by one or a number of oxygen atoms, and X is a carboxylic, sulfuric or phosphoric acid residue or a radical including a carboxylic acid or an amide group;

b) amine oxides of formula

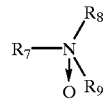

in which $R_7$ denotes a $C_{16}$–$C_{22}$ alkyl and $R_8$ and $R_9$, in which are identical or different, represent a $C_1$–$C_4$ alkyl or $C_1$–$C_4$ hydroxyalkyl;

c) biopolysaccharides.

16. Composition according to claim 1 wherein the cosmetically acceptable medium consists of water or a mixture of water and of a cosmetically acceptable solvent.

17. Composition according to claim 1 which contains additives selected from the group consisting of foam reinforcers, sequestering agents, electrolytes, fragrances, preservatives, fatty alcohols, minera, vegetable, animal and synthetic oils and waxes, ceramides, UV screening agents, pearlescence agents, agengs for combating free radicals, biocides, antibacterials, antidandruff, antiseborrheic and antiparasitic agents, repellents, dyes, pigments, oxidizing agents, reducing agents, moisturizers, anionic and nonionic polymers, vitamins and α-hydroxy acids.

18. Process for cosmetic washing and/or conditioning of hair or skin, which consists in applying an effective amount of a composition according to claim 1 to the skin or the hair, this application optionally being followed by rinsing with water.

* * * * *